United States Patent [19]

Berg

[11] Patent Number: 4,836,896

[45] Date of Patent: Jun. 6, 1989

[54] SEPARATION OF M-DIISOPROPYLBENZENE FROM P-DIISOPROYLBENZENE BY AZEOTROPIC DISTILLATION WITH ACETOPHENONE

[75] Inventor: Lloyd Berg, 1314 S. Third Ave., Bozeman, Mont. 59715

[73] Assignee: Lloyd Berg, Bozeman, Mont.

[21] Appl. No.: 294,483

[22] Filed: Jan. 9, 1989

Related U.S. Application Data

[63] Continuation-in-part of Ser. No. 270,200, Nov. 14, 1988.

[51] Int. Cl.$^4$ .......................... B01D 3/38; C07C 7/06
[52] U.S. Cl. ......................................... 203/46; 203/62; 568/335; 585/808; 585/835; 585/839; 585/864
[58] Field of Search ............................. 203/62, 54, 46; 585/804, 807, 808, 835, 836, 839, 864; 568/335

[56] References Cited

U.S. PATENT DOCUMENTS

| | | | |
|---|---|---|---|
| 2,398,689 | 4/1946 | Bloomer | 203/46 |
| 2,461,993 | 2/1949 | McKinnis | 203/62 |
| 2,805,258 | 9/1957 | Boodman | 585/839 |
| 2,840,621 | 6/1958 | Corson et al. | 585/839 |
| 3,222,349 | 12/1965 | Holder | 585/804 |
| 4,128,594 | 12/1978 | Westernacher | 585/806 |

FOREIGN PATENT DOCUMENTS

| | | | |
|---|---|---|---|
| 49-47326 | 5/1975 | Japan | 585/866 |
| 50-70324 | 6/1975 | Japan | 585/864 |

*Primary Examiner*—Wilbur Bascomb

[57] ABSTRACT

Meta- and para-diisopropylbenzenes cannot be easily separated from each other by distillation because of the closeness of their vapor pressures. m-Diisopropylbenzene can be readily removed from p-diispropylbenzene by azeotropic distillation using acetophenone. The acetophenone - m-diisopropylbenzene azeotrope can be separated by solvent extraction with propylene glycol to remove the acetophenone and the propylene glycol - acetophenone mixture is readily separated from each other by rectification.

1 Claim, No Drawings

SEPARATION OF M-DIISOPROPYLBENZENE FROM P-DIISOPROYLBENZENE BY AZEOTROPIC DISTILLATION WITH ACETOPHENONE

This is a continuation in part of application Ser. No. 07/270,200, filed Nov. 14, 1988.

FIELD OF THE INVENTION

This invention relates to a method for separating m-diispropylbenzene from p-diisopropylbenzene using acetophenone as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile compound comes off as bottoms product. The usual methods of separating the azeotrope former from the more volatile component are cooling and phase separation or solvent extraction.

In the manufacture of cumene, also called isopropylbenzene, by the alkylation of benzene with propylene, the most prevalent by-products are the diisopropylbenzenes with the meta and para isomers comprising most of the by-product. m-Diisoproylbenzene (m-DIPB) boils at 203.2° C. p-Diisopropylbenzene (p-DIPB) boils at 210.3° C. and these two have a relative volatility of 1.14. The difficulty of separating these two by rectification can be shown by the data in Table 1. Table 1 shows that rectification of m-DIPB from p-DIPB in 99% purity requires 95 actual plates. Using azeotropic distillation with an agent yielding a relative volatility of 1.45 would require only 34 actual plates. Thus azeotropic distillation would be an attractive method of effecting the separation of these isomers if agents can be found that (1) will increase the relative volatility of m-DIPB to p-DIPB and (2) are easy to recover from the p-DIPB.

TABLE 1

| Plates Required To Effect Separation in 99% Purity | | |
|---|---|---|
| Relative Volatility | Theoretical Plates | Actual Plates, 75% Efficiency |
| 1.14 | 71 | 95 |
| 1.22 | 47 | 63 |
| 1.25 | 41 | 55 |
| 1.37 | 29 | 39 |
| 1.45 | 25 | 34 |

Azeotropic distillation typically requires the addition of about as much agent as m-DIPB to be boiled up in the column which increases the heat requirement as well as somewhat larger diameter plates to accomodate the increase in liquid and vapor in the column. In addition, a solvent extraction column is usually provided to recover and recycle the azeotrope forming agent.

OBJECTIVE OF THE INVENTION

The objective of this invention is to provide a process or method of azeotropic distillation that will enhance the relative volatility of m-DIPB from p-DIPB in their separation in a rectification column using acetophenone as the azeotrope forming agent. It is a further object of this invention to identify a compound which will remove acetophenone from m-DIPB by solvent extraction and which can be separated from acetophenone by ordinary rectification.

SUMMARY OF THE INVENTION

The objects of this invention are provided by a process for separating m-DIPB from p-DIPB which entails the use of acetophenone in an azeotropic distillation process, followed by the separation of the m-DIPB-acetophenone azeotrope by solvent extraction with propylene glycol.

DETAILED DESCRIPTION OF THE INVENTION

I have discovered that acetophenone will effectively enhance the relative volatility of m-DIPB from p-DIPB and permit the separation of m-DIPB from p-DIPB by rectification when employed as the agent in azeotropic distillation. When allowed to come to equilibrium in a vapor-liquid equilibrium still, acetophenone was found to increase the relative volatility of m-DIPB to p-DIPB to 1.45. I found that when the m-DIPB-acetophenone azeotrope was extracted with propylene glycol (also called 1,2-propanediol), the propylene glycol would dissolve out the acetophenone but leave the m-DIPB unaffected.

THE USEFULNESS OF THE INVENTION

The usefulness or utility of this invention is that when acetophenone is employed as the azeotrope former, the column plate requirement is reduced from 95 to 34 and when propylene glycol is employed as the solvent in solvent extraction, the azeotrope is broken and the acetophenone and propylene glycol can be separated by rectification and recycled.

WORKING EXAMPLES

Example 1

Forty grams of m-DIPB-p-DIPB mixture and 40 grams of acetophenone were charged to an Othmer type vapor liquid equilibrium still and refluxed for six hours. The azeotrope boiled at 191° C. (640 mm) and contained about 60% acetophenone. Both the vapor and liquid portions from the vapor-liquid equilibrium still were then extracted with propylene glycol at room temperature. Two liquid phases were obtained. The hydrocarbon phase was analysed by gas chromatography which gave a vapor composition of 69.5% m-DIPB, 30.5% p-DIPB and a liquid composition of 61.1% m-DIPB, 38.9% p-DIPB. This is a relative volatility of m-DIPB to p-DIPB of 1.45. The propylene glycol-acetophenone liquid phase was rectified and gave propylene glycol at 181° C. as overhead and acetophenone boiling at 194° C. as bottoms. Both were ready for recycle.

I claim:

1. A process for recovering m-diisopropylbenzene from a mixture of m-diisopropylbenzene and p-diisopropylbenzene which comprises (1) distilling a mixture of m-diisopropylbenzene and p-diisopropylbenzene in a rectification column in the presence of acetophenone as an azeotrope forming agent, recovering a m-diisopropylbenzene-acetophenone azeotrope as overhead product, obtaining the p-diisopropylbenzene from the still-pot, (2) subjecting the m-diisopropylbenzene-acetophenone azeotrope to solvent extraction with propylene glycol at ambient temperature to form two immiscible liquid phases, recovering the m-diisopropylbenzene as the hydrocarbon phase and the acetophenone and the propylene glycol as the glycol phase, (3) separating the acetophenone from the propylene glycol by rectification.

* * * * *